(12) United States Patent
Wilberg et al.

(10) Patent No.: US 8,382,808 B2
(45) Date of Patent: Feb. 26, 2013

(54) BONE SCREW

(75) Inventors: Lothar Wilberg, Bühlertann (DE);
Roland Eberlein, Niederwürschnitz (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 29 days.

(21) Appl. No.: 12/763,095

(22) Filed: Apr. 19, 2010

(65) Prior Publication Data
US 2010/0298889 A1 Nov. 25, 2010

Related U.S. Application Data

(63) Continuation of application No. 10/399,066, filed as application No. PCT/EP00/09062 on Sep. 16, 2000, now Pat. No. 7,717,947.

(30) Foreign Application Priority Data

Oct. 12, 1999 (DE) .................................. 199 49 285

(51) Int. Cl.
*A61B 17/86* (2006.01)
(52) U.S. Cl. ...................................... 606/304; 411/82.1
(58) Field of Classification Search .......... 606/300–331, 606/92–94; 411/82.1, 395
See application file for complete search history.

(56) References Cited

U.S. PATENT DOCUMENTS

| | | | |
|---|---|---|---|
| 4,484,570 A | 11/1984 | Sutter et al. | |
| 4,653,489 A | 3/1987 | Tronzo | |
| 4,760,844 A * | 8/1988 | Kyle | 606/65 |
| 4,860,513 A * | 8/1989 | Whitman | 52/410 |
| 5,047,030 A | 9/1991 | Draenert | |
| 5,084,050 A | 1/1992 | Draenert | |
| 5,129,904 A | 7/1992 | Illi | |
| 5,143,498 A * | 9/1992 | Whitman | 411/82 |
| 5,145,301 A * | 9/1992 | Yamamoto | 411/82 |
| 5,192,282 A | 3/1993 | Draenert | |
| 5,249,899 A * | 10/1993 | Wilson | 411/82 |
| 5,484,442 A | 1/1996 | Melker et al. | |
| 5,743,912 A | 4/1998 | Lahille et al. | |
| 5,788,702 A * | 8/1998 | Draenert | 606/92 |
| 5,868,749 A * | 2/1999 | Reed | 606/76 |
| 5,871,484 A | 2/1999 | Spievack et al. | |
| 5,968,047 A | 10/1999 | Reed | |
| 5,971,987 A | 10/1999 | Huxel et al. | |

(Continued)

FOREIGN PATENT DOCUMENTS

| | | |
|---|---|---|
| CH | 672245 | 11/1989 |
| DE | 35 08 759 A1 | 10/1985 |

(Continued)

OTHER PUBLICATIONS

Raymond G. Tronzo, M.D., Augment Internal Fixation With Fenestrated Hip Screw and Cement, Orthopaedic Review, vol. XII, No. 4, Apr. 1983, pp. 59-64.

*Primary Examiner* — Kevin T Truong
*Assistant Examiner* — Michael Araj
(74) *Attorney, Agent, or Firm* — Christie, Parker & Hale, LLP

(57) ABSTRACT

A bone screw has a screw head and a threaded shank. An axial bore into which a plurality of radial bores set at a distance from each other open, extends through the threaded shaft. The axial bore is open at the screw head side end, and the radial bores are also open at the radially outer end. The axial bore is closed in an axial direction in the area of the end of the screw shank that lies opposite the screw head.

1 Claim, 3 Drawing Sheets

U.S. PATENT DOCUMENTS

| | | |
|---|---|---|
| 6,048,343 A | 4/2000 | Mathis et al. |
| 6,210,376 B1 * | 4/2001 | Grayson .................. 604/264 |
| 6,214,012 B1 | 4/2001 | Karpman et al. |

FOREIGN PATENT DOCUMENTS

| | | |
|---|---|---|
| DE | 197 41 087 A1 | 4/1999 |
| DE | 299 14 192 U1 | 11/1999 |
| EP | 0 490 517 B1 | 6/1992 |
| EP | 0682917 A1 | 11/1995 |
| GB | 2 157 177 A | 10/1985 |
| JP | 07051292 A | 2/1995 |
| JP | 07222752 A | 8/1995 |
| JP | 09149906 A | 6/1997 |
| JP | 10211213 A | 8/1998 |
| WO | WO 00/28907 | 5/2000 |
| WO | WO 01/76494 A1 | 10/2001 |

* cited by examiner

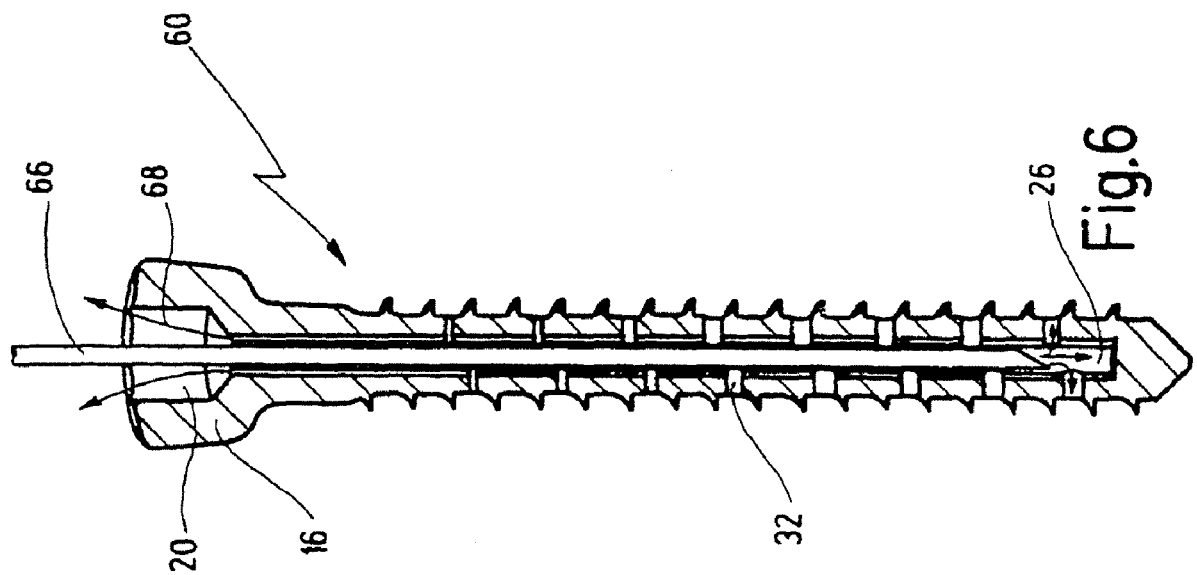
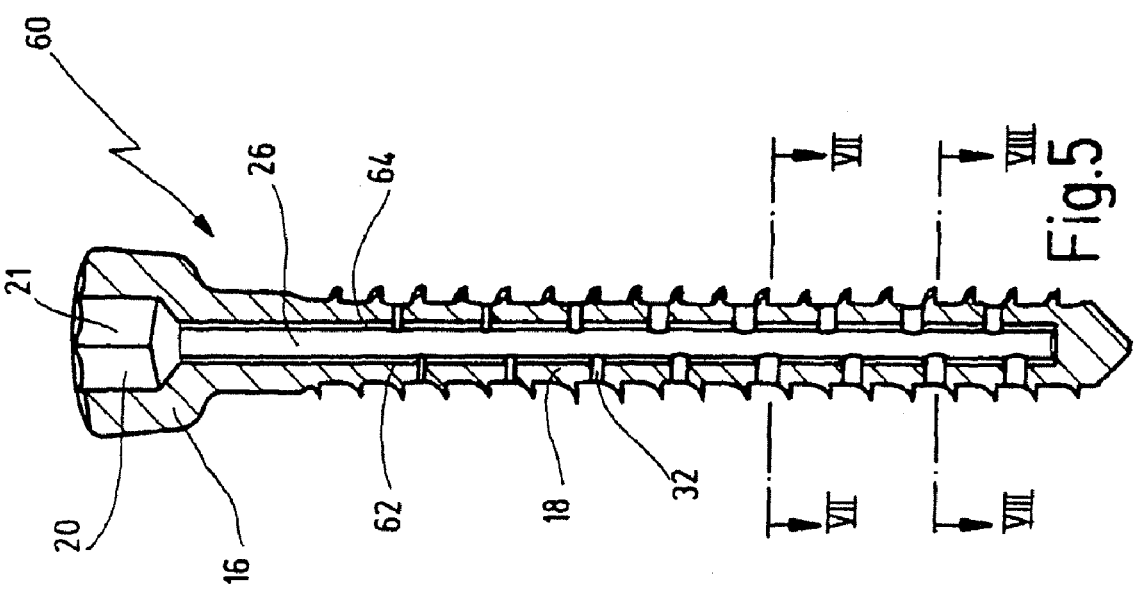
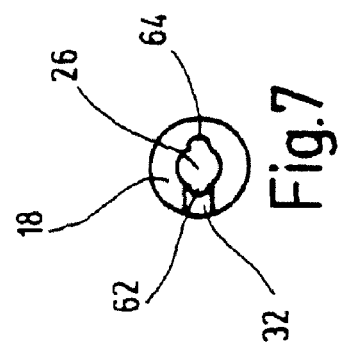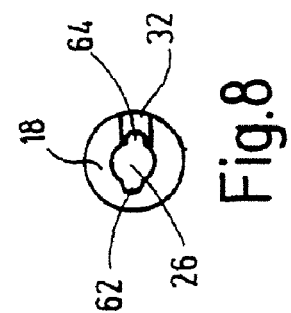

BONE SCREW

CROSS-REFERENCE TO RELATED APPLICATION(S)

This application is a continuation of U.S. application Ser. No. 10/399,066 filed Nov. 12, 2003 now U.S. Pat. No. 7,717,947, which is a National Phase Patent Application and claims the priority of International Application Number PCT/EP00/09062, filed on Sep. 16, 2000, which claims priority of German Patent Application Number 199 49 285.9, filed on Oct. 12, 1999.

SUMMARY OF THE INVENTION

The invention relates to a bone screw that comprises a screw head and a threaded shank, wherein an axial bore into which a plurality of radial bores set at a distance from each other open, extends through the threaded shaft, and said axial bore is open at the screw head side end, the radial bores each also being open at the radially outer end.

A like bone screw is known from U.S. Pat. No. 5,192,282.

In the course of the surgical treatment of bone fractures of the human skeleton, for example, a bone screw of the aforementioned type is intended to attach a bone fixation plate to the fractured bone in order to immobilize the fractured bone, thus allowing it to grow together again. Usually, such bone screws and the bone fixation plate are made of medical grade stainless steel or titanium.

The bone fixation plate comprises several bores, through each of which one bone screw is screwed into the bone. After the bone screw has been screwed into the bone completely, the screw head is countersunk in the bone fixation plate and fixed as free from play as possible.

The bone screw comprises a threaded shank with a self-cutting thread that drives itself into the bone, thus ensuring the thrust of the screw into the bone.

After the bone screw has been screwed into the bone, the bone fixation plate must be fixed to the bone, as permanently and free from play as possible. This is also dependent on the support the bone screw itself finds in the bone into which it is screwed. Normally, the support of the screw in the bone is improving in the course of time by bone growing, thus causing bony tissue to form around the threaded shank of the bone screw and to adhere to same on all sides.

This, however, can only be observed in younger patients with a healthy bone structure. In elderly patients, bony growth and, thus, the formation of bony tissue is strongly reduced. In case of osteoporosis patients, the situation is even more problematic, since such patients are, in addition, suffering from a decrease in bony substance with an increased susceptibility to fractures.

In such critical cases, the bony tissue fails to give any permanent support to the bone screw. For that reason, the bone screw requires reliable fixation in the bone by being cemented in the bone with bone cement.

Usually, a like bone cement is made from polymethyl methacrylate or related compounds. Normally, the bone cement, when being in the processing state, is available as paste or as high-viscosity fluid.

At present, the procedure of cementing a bone screw in the bone comprises smearing of the threaded shank with bone cement and then screwing it into the bone. When the screw is screwed in, however, the major part of the cement is stripped from the threaded shank, thus being prevented from entering into the bone at all.

Predrilling the screw hole and filling the cement into the bone beforehand is likewise of disadvantage because the bone cement is pressed out of the drilled hole when the bone screw is screwed in. Moreover, predrilling of the screw hole is not desired in most of the cases.

The bone screw known from the aforementioned U.S. Pat. No. 5,192,282 comprises a screw head and a threaded shank. An axial bore that passes completely through the screw, thus being open at either end, extends through the threaded shank. A plurality of radial bores that are open at their radially outer end extend from the axial bore.

This known bone screw is intended to evacuate air and liquids from the bone into which it is screwed, by connecting a vacuum pump to the screw head by means of an appropriate device.

The vacuum is intended to cause the bone cement that has been injected into the bone at a different place to distribute and spread in the bony tissue in an improved manner.

Moreover, the bone screw is intended to put liquid drugs into the bone therethrough. Although it is, in principle, suitable, the bone screw is not intended to attach the bone fixation plate to the bone. Neither is the bone screw itself cemented in the bone; instead, the cement mentioned is used to cement an endoprosthesis that is implanted at a different place of the bone.

The invention aims at further developing a bone screw of the aforementioned type in such a manner that it can be reliably and permanently anchored in the bone by means of bone cement.

This problem is solved by the invention in that the axial bore is closed in an axial direction in the area of the end of the threaded shank that is located opposite the screw head.

The embodiment of the bone screw according to the invention permits screwing of the bone screw into the bone in the usual manner. Owing to the embodiment according to the invention, bone cement can then be injected through the axial bore and the radial bores being in communication therewith, that is to say through the screw and into the bone, with the bone cement spreading over the region around the threaded shank of the bone screw. The fact that the axial bore is closed in an axial direction at the end that is located opposite the screw head, thus being formed as a blind hole bore, is of advantage in that the bone cement exits only from the radial bores. In contrast to the embodiment of the known bone screw, the bone cement is, hence, prevented from exiting in an axial direction from the end of the threaded shank that is located opposite the screw head and entering into the bone, where the bone cement is not able to help anchor the bone screw. Since, while the bone screw is being screwed in, the radial pressure of the bony tissue on the bone screw is higher than the axial pressure on the tip of the threaded shank, the bone cement, if injected through the known bone screw, would mainly exit from the tip, because the radially adjacent bony tissue offers a higher resistance to the exiting of the bone cement from the radial bores than at the axial end of the axial bore. The embodiment according to the invention, however, ensures that the bone cement exits only in a radial direction, thus being able to environ the threaded shank and to cement same in the bone.

In a preferred embodiment, an aperture cross-section of the individual radial bores is increasing towards the end of the threaded shank that is located opposite the screw head.

In this embodiment, a radial bore that is set at a distance from the screw head is provided with an aperture cross-section that exceeds that of a radial bore that is set near the screw head. This is of advantage in that, on the one hand, it is possible to inject more bone cement in the surrounding bony tissue in deeper regions of the bone where the end of the threaded shank that is located opposite the screw head is finally placed when the bone screw is screwed in, whereby it is ensured that the screw is anchored in a particularly reliable manner in the area of its end that is placed deeply in the bone. Furthermore, when the bone cement is injected through the larger aperture cross-sections of the radial bores at the end that is located opposite the screw head, the higher exiting resistance present there is accounted for by the surrounding tissue, so that it is possible to inject the bone cement in the bony tissue with a more uniform exiting resistance over the entire threaded shank.

In a further preferred embodiment, an adapter that can be fitted onto the screw head in a tight manner is provided, wherein said adapter comprises an axial bore that is aligned with the axial bore of the threaded shank when said adapter is in the fitted state and wherein said adapter comprises a holder for taking up a lower syringe or cartridge end in a tight manner.

Using this adapter for injecting the bone cement through the bone screw and into the bony tissue is of the particular advantage that the bone cement can be injected through the screw and into the bone from a syringe or cartridge at a very high pressure, so that the bone cement is pressed into the porous bony tissue. That is to say that the adapter that is sealing in an air-tight manner prevents the bone cement, when being injected into the screw, from exiting from same through the screw head. Tests have shown that the use of the adapter permits to apply such high injection pressures that the bone cement can be reliably injected through the screw even into bony tissue having a higher density. But the adapter not only permits injection of the bone cement under pressure, but also controlled-dosage injection of selected volumes of bone cement.

Here, the adapter is preferably made of a plastic material.

A plastic adapter is of advantage in that it has certain clinging properties, so that the adapter can be caulked perfectly with the screw head, thus ensuring an entirely airtight fit of the adapter on the screw head.

In a further preferred embodiment, the screw head comprises a holder, and a lower end of the adapter is formed in a complementary manner with the holder.

This measure is also of advantage in that it helps fit the syringe or cartridge that is filled with the bone cement to the screw head in a tight manner, because the adapter of this embodiment can be inserted in the screw head in a positive manner. Another advantage is that the adapter can be fixed to the screw head in a particularly easy manner and that it is held on the screw head without requiring any additional safety measures, such as clamping or the like. This ensures that the bone cement can be injected into the bone screw in a particular reliable manner as regards handling.

In further preferred embodiments, the adapter comprises a circumferential shoulder that is supported on the screw head with the adapter being in the fitted state, and/or the holder of the adapter for taking up the lower syringe or cartridge end comprises a circumferential shoulder.

These above-mentioned measures are also of advantage in that they help fit the adapter tightly to the screw head, so that the bone cement can be injected through the bone screw and into the bony tissue surrounding the threaded shank at high pressure.

In a further preferred embodiment, the axial bore in the threaded shank comprises at least one eccentric radial extension, which extends along the length of the axial bore.

This eccentric radial extension of the axial bore can be used as an air escape duct in case the bone cement is prefilled into the axial bore of the bone screw by means of a syringe cannula that is completely inserted in the axial bore. In this ease, a syringe cannula is used to fill bone cement into the bone screw that has already been screwed into the bone, initially without the above-mentioned adapter, until the axial bore and the radial bores are prefilled with bone cement, if possible free from air. Subsequently, the above-mentioned adapter can be used to press the bone cement into the bony tissue under high pressure.

Preferably and to advantage, the radial bores open into the eccentric extension of the at least one axial bore.

In a further preferred embodiment, the radial bores are distributed uniformly both in axial and in circumferential direction.

In this manner, a uniform hedgehog-shaped exit of the bone cement into the bony tissue is achieved.

In a further preferred embodiment, the radial bores open between the thread flanks of the threaded shaft at their radially outer end.

This is of advantage in that the radial bores do not interrupt the thread and do, thus, not affect the process of screwing the bone screw into the bone.

Further advantages can be seen from the following description and the appended thawing.

It is understood that the elements mentioned above and still to be explained below can be used not only in the particular combination specified, but also in other combinations or autonomously, without departing from the scope of the present invention.

BRIEF DESCRIPTION OF THE DRAWINGS

Executive examples of the invention are illustrated in the drawing and explained in more detail in the description below, wherein

FIG. 5 is a longitudinal cross-sectional view of a further bone screw according to an executive example that has been modified to a minor degree;

FIG. 6 is a view of the bone screw of FIG. 5 while bone cement is being prefilled by means of a syringe cannula;

FIG. 7 is a sectional view taken from lines VII-VII in FIG. 5; and

FIG. 8 is a sectional view taken from lines VIII-VIII in FIG. 5.

FIGS. 1 and 4 show a bone screw generally referred to with reference mark 10.

DETAILED DESCRIPTION OF THE INVENTION

Figure 4:
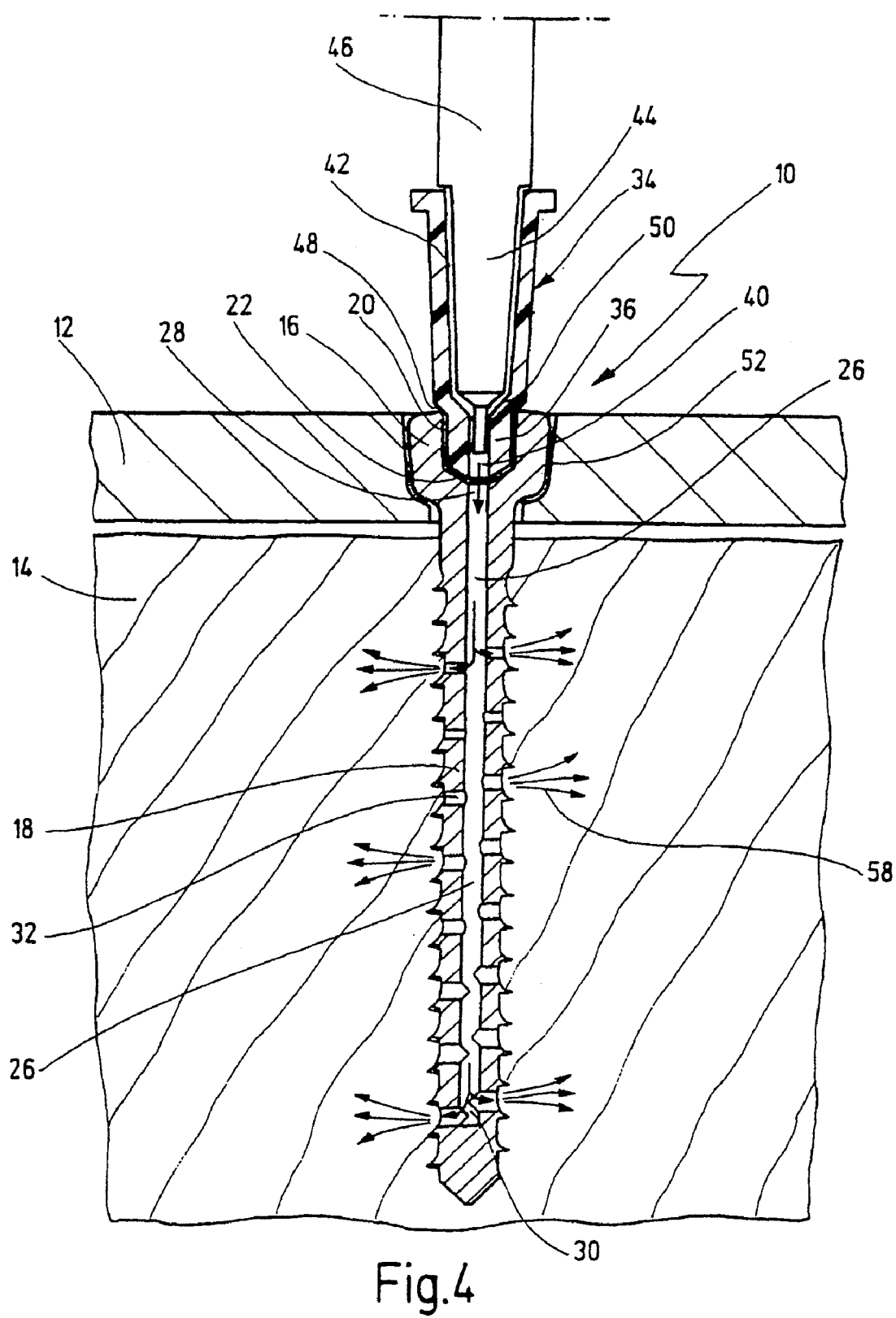
FIG. 4 is a view of the configuration comprising the bone screw, the adapter and the syringe while bone cement is being injected.

The bone screw 10 is intended to attach a bone fixation plate 12 to a bone 14 of the human skeleton, as shown in FIG. 4.

As will still be described below, the bone screw 10 permits the injection of bone cement into the bone 14 and, thus, cementing of the bone screw 10 in the bone 14.

The bone screw 10 comprises a screw head 16 that is connected to a threaded shank 18 in a single piece.

Altogether, the bone screw 10 is made of medical grade stainless steel or of titanium.

The screw head 16 has a circular outer circumference, with the diameter of the screw head 16 slightly reducing towards the threaded shank 18.

The screw head 16 comprises a central opening 20 that is designed as a hexagon socket, as shown in the executive example of FIG. 5. The opening 20 having the shape of a hexagon socket is provided for holding an appropriately designed Allen wrench while the bone screw 10 is being screwed into the bone 14.

At its end adjacent to the threaded shank 18, the opening 20 is reduced conically in its diameter and is provided with a circular circumference within the area of this end 22.

At its outer circumference, the threaded shank 18 comprises a thread with a plurality of thread flanks 24. The threaded shank 18 is provided with an approximately uniform outer diameter over its entire length.

An axial bore 26 that is open at its screw head side end 28, that is to say that ends in the opening 20 of the screw head 16, extends through the threaded shank 18.

At an end 30 that is located opposite the screw head 16, however, the axial bore 26 is closed in an axial direction, so that the axial bore 26 is formed as a blind hole bore in the threaded shank 18.

The axial bore 26 is arranged centrally in the threaded shank 18 and extends substantially with the same circular opening cross-section over the entire length of the threaded shank 18.

Furthermore, a plurality of radial bores 32 set at a distance from each other are provided in the threaded shank 18, with said radial bores 32 opening into the axial bore 26, thus being in communication therewith. At their radially outer end, each of the radial bores 32 are open.

The radial bores 32 are uniformly distributed over the threaded shank 18, both in axial and in circumferential direction. In circumferential direction, the radial bores 32 are offset in relation to each other by 90 degrees or even by 180 degrees. Here, the number of the radial bores 32 is not a critical factor, but should be as high as possible.

Figure 1:
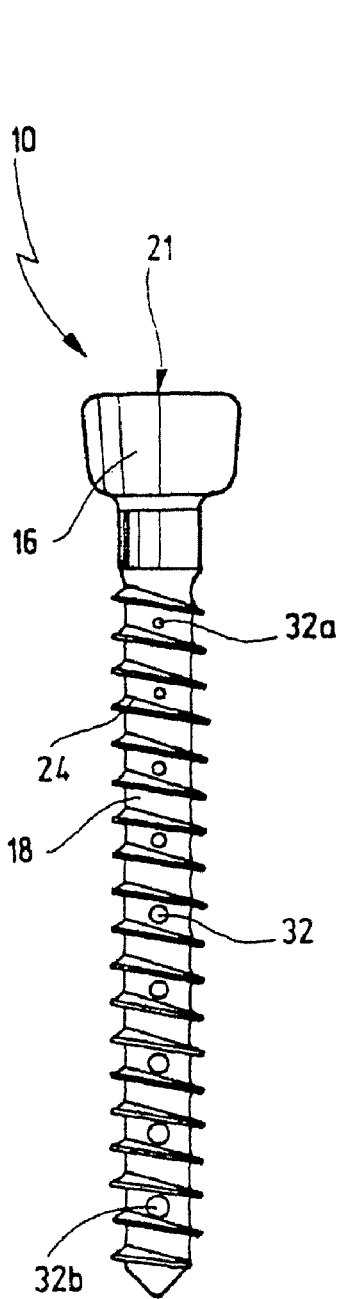
FIG. 1 is a lateral view of the bone screw.

As is shown in FIGS. 1 and 4, an aperture cross-section of the individual radial bores 32 increases from the screw head side end of the threaded shank 18 towards the end of the threaded shank 18 that is located opposite the screw head 16. In other words, an aperture cross-section of a radial bore 32a shown in FIG. 1 is smaller than a cross-section of a radial bore 32b shown in FIG. 1.

FIGS. 1 and 4 furthermore show that each of the radial bores 32 is arranged between the thread flanks 24 of the thread of the threaded shank 18.

Figure 2:
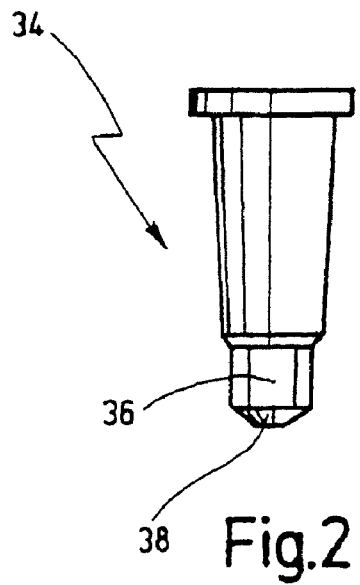
FIG. 2 is a lateral view of an adapter to be used with the bone screw of FIG. 1.

Moreover, an adapter 34 that is shown autonomously in FIG. 2 is provided for the bone screw 10.

The adapter 34 is made of a plastic material.

The adapter 34 can be fitted onto the screw head 16 of the bone screw 10 in a tight manner, that is to say, in the executive example shown, a lower end 36 of the adapter 34, with regard to its outer contour, is designed complementarily with the inner contour of the opening 20 of the screw head 16, with said opening 20 forming a holder 21 (cf. FIG. 5) for the adapter 34. Accordingly, the lower end 36 of the adapter 34 comprises an external hexagon as well as a conical tip 38 that is adjacent to the external hexagon in a downward direction, with said conical tip 38 being designed complementarily with the end 22 of the opening 20 of the screw head 16.

Hence, the function of the opening 20 of the bone screw 10 is not only to hold the operation-side end of an Allen wrench while the bone screw 10 is being screwed into the bone 14, but also to hold the lower end 36 of the adapter 34 in an at least fluid-tight, but preferably air-tight manner, after the bone screw 10 has been screwed into the bone 14.

The adapter 34 comprises an axial bore 40 that is aligned with the axial bore 26 of the bone screw 10, with the adapter 34 being fitted onto the screw head 16.

Figure 3:
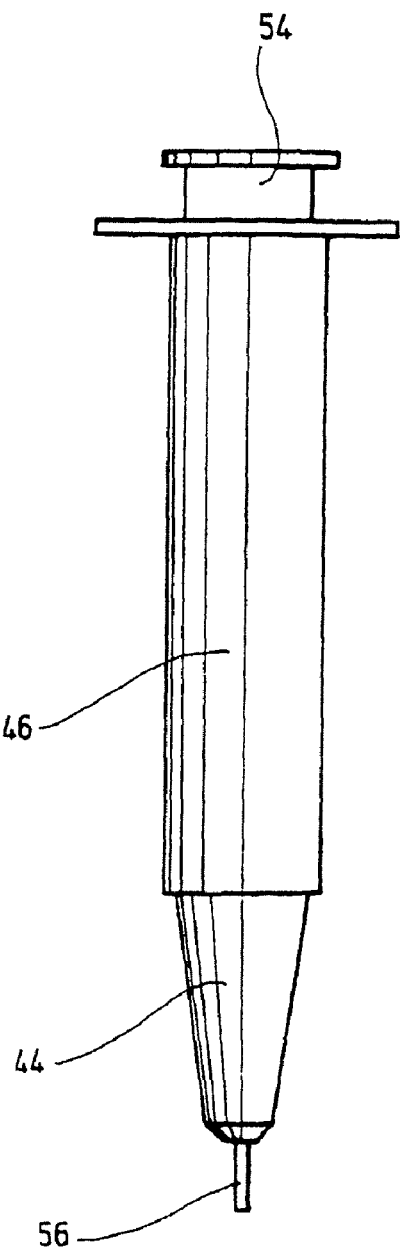
FIG. 3 is a lateral view of a syringe for injection of bone cement into the bone screw of FIG. 1 with use being made of the adapter of FIG. 2.

The adapter 34, in turn, comprises a holder 42 to take up a lower end 44 of a syringe 46 shown in FIG. 3. For example, the syringe 46 is a syringe as it is usually used for medical purposes. For the purposes of the invention, it is also possible to use a cartridge instead of the syringe 46.

In order to further improve the tightness of the fit of the adapter 34 in the opening 20 of the screw head 16, the adapter 34 comprises a shoulder 48 along its outer circumference, with said shoulder 48 being supported on the screw head 16 at the upper end of the opening 20.

In order that the adapter 34 is also able to take up the lower end 44 of the syringe 46 in as air-tight a manner as possible, the holder 42 of the adapter 34 comprises a shoulder 50 along its inner circumference, with said shoulder 50 being designed with a slope and, thus, conically with regard to the axial direction.

Below follows a more detailed description of how to handle the bone screw 10 in connection with the adapter 34 and the syringe 46 for attaching the bone fixation plate 12 and for injection of bone cement into the bone 14.

In the usual manner, the bone screw 10 is screwed into the bone 14 through an opening 52 and through the bone fixation plate 12, until the screw head 16 is countersunk in the opening 54 of the bone fixation plate 12.

Subsequently, the adapter 34 is inserted in the opening 20 and in the screw head 16 with its lower end 36. Owing to the complementary design of the lower end 36 of the adapter 34, the lower end 36 is held positively in the opening 20, thus being already locked in position without having to be held manually.

Subsequently, the syringe 46 is inserted in the holder 42 of the adapter 34 with its lower end 44. By exerting slight pressure on the syringe 46, the lower end 44 of the syringe 46 is, on the one hand, held tightly in the holder 42 and, on the other hand, the lower end 36 of the adapter 34 is held tightly in the opening 20 of the screw head 16.

To achieve this, the adapter 34 is preferably made of a more or less resilient plastic material, so that the above-mentioned parts can be well-caulked with regard to each other, thus forming a mutually tight closure.

By actuating a syringe plunger 54 of the syringe 46 that has been filled with bone cement beforehand, bone cement is now injected from a tip 56 of the syringe 46, that is finally placed in the axial bore 40 of the adapter 34 as shown in FIG. 4, into the axial bore 26 and into the radial bores 32 in the threaded shank 18 of the bone screw 10.

Owing to the sealing function of the adapter 34, the bone cement can be injected into the axial bore 26 and into the radial bores 32 at a very high pressure, without permitting the bone cement to exit from the top of the bone screw 10. Here, the pressure applied can be so high that the exiting resistance present at the radially outer ends of the radial bores 32, that is caused by the adjacent bony tissue of the bone 14, is overcome, so that the bone cement exits into the bone 14 uniformly, as is indicated by the bundles of arrows 58.

The fact that the opening cross-sections of the radial bores 32 are increasing towards the end of the threaded shank 18 that is located opposite the screw head 16 ensures that a sufficient volume of bone cement exits from the radial bores 32 and into the bone 14 even in deeper regions of the bone. As viewed along the entire threaded shank 18, the bone cement exits from the radial bores 32 in an approximately hedgehog-shaped manner. The adapter permits controlled-dosage injection of selected volumes of bone cement into the bone 14.

After a sufficient volume of bone cement has been injected into the bone 14, the syringe 46 and the adapter 34 are removed from the bone screw 10.

FIGS. 5 through 8 show a bone screw 60 that is slightly modified in comparison with the bone screw 10. Where the bone screw 60 is provided with the same features as the bone screw 10, the same reference marks have been used as in FIGS. 1 through 4.

The bone screw 60 is different from the bone screw 10 in that the axial bore 26 in the threaded shank 18 comprises at least one, here two radial eccentric extensions 62 and 64 that are arranged opposite to each other. The eccentric extensions 62 and 64 are provided with a different radius than the axial bore 26.

As shown in FIGS. 7 and 8, the radial bores 32 are each leading to one of the eccentric extensions 62 and 64. The main cross-section of the axial bore 26, however, is circular and approximately corresponds with the diameter of a syringe cannula 66 that can, for example, be fitted onto the syringe 56 of the syringe 46 shown in FIG. 3.

The procedure regarding the bone screw 60 is as described below.

First, the bone screw 60 is again screwed through the bore 52 of the bone fixation plate 12 and completely into the bone 14, as described with regard to FIG. 4.

Subsequently, a syringe cannula 66 is completely pushed into the axial bore 26 of the bone screw 60. Subsequently, bone cement is injected through the syringe cannula 66 and into the axial bore 26, wherein the syringe cannula 66 is gradually pulled out of the axial bore 26 while this procedure is in progress. Here, air that is displaced when the bone cement is injected can escape through the eccentric extensions 62 and 64 and out of the opening 20, as indicated by the arrows 68 in FIG. 6. In this manner, the axial bore 26 as well as the radial bores 32 can, initially, be filled completely with bone cement, until air is no longer present in any of the bores.

Subsequently, the syringe cannula 66 is completely pulled out of the axial bore 26 and removed from the syringe 46. Subsequently, the procedure can be continued as described with regard to FIG. 4, that is to say additional bone cement is injected through the axial bore 26 and the radial bores 32 and into the bone 14 at high pressure. The fact that all of the air has been pressed out of the bores 26 and 32 beforehand, now causes a uniform static pressure in all bores 26 and 32 while the bone cement is being injected, with this pressure being exerted by the syringe 46 while the bone cement is being injected. In this manner, it is ensured that the bone cement exits from the radial bores 32 in a manner that is even more uniform. Here, the adapter 34 closes the radial extensions 62 and 64 at their screw head side end.

What is claimed is:

1. A bone screw, comprising a screw head and a threaded shank, wherein an axial bore into which a plurality of radial bores open which are set at a distance from each other, extends through the threaded shank, wherein said axial bore is open at the screw head side end and wherein the radial bores are also open at the radially outer end, wherein the axial bore is closed in an axial direction in the area of the end of the threaded shank that is located opposite the screw head, wherein an aperture cross-section of the various radial bores is increasing towards the end of the threaded shank that is located opposite the screw head.

* * * * *